US012800605B2

(12) United States Patent
Kim et al.

(10) Patent No.: US 12,800,605 B2
(45) Date of Patent: Nov. 17, 2026

(54) CONTAMINANT ANALYSIS APPARATUS AND WATER QUALITY MONITORING SYSTEM

(71) Applicant: Samsung Electronics Co., Ltd., Suwon-si (KR)

(72) Inventors: Yeontae Kim, Suwon-si (KR); Jinhee Park, Suwon-si (KR); Joengseok Kim, Daejeon (KR); Jinseop Lee, Daejeon (KR); Bongkyun Jin, Daejeon (KR); Eunju Park, Suwon-si (KR); Eungsun Lee, Daejeon (KR); Hyekyoung Moon, Suwon-si (KR); Hyangbong Lee, Suwon-si (KR); Hyunyul Park, Suwon-si (KR); Seoungkyo Yoo, Daejeon (KR)

(73) Assignees: SAMSUNG ELECTRONICS CO., LTD.; Withtech Inc, Yuseong-gu Daejeon (KR)

( * ) Notice: Subject to any disclaimer, the term of this patent is extended or adjusted under 35 U.S.C. 154(b) by 340 days.

(21) Appl. No.: 18/432,494

(22) Filed: Feb. 5, 2024

(65) Prior Publication Data

US 2024/0264194 A1 Aug. 8, 2024

(30) Foreign Application Priority Data

Feb. 8, 2023 (KR) ........................ 10-2023-0017033

(51) Int. Cl.
*G01N 35/10* (2006.01)
*G01N 33/18* (2006.01)
*G01N 35/08* (2006.01)

(52) U.S. Cl.
CPC ..... *G01N 35/1095* (2013.01); *G01N 33/1813* (2013.01); *G01N 35/085* (2013.01); *G01N 35/1016* (2013.01)

(58) Field of Classification Search
CPC .............................. G01N 33/1813; C02F 1/62
See application file for complete search history.

(56) References Cited

U.S. PATENT DOCUMENTS

| | | | | |
|---|---|---|---|---|
| 4,472,354 A * | 9/1984 | Passell | .................. | G01N 33/18 422/62 |
| 4,545,957 A * | 10/1985 | Vanhumbeeck | ... | G01N 33/1813 422/81 |

(Continued)

FOREIGN PATENT DOCUMENTS

| | | |
|---|---|---|
| CN | 106290217 A | 1/2017 |
| CN | 115032030 A | 9/2022 |

(Continued)

*Primary Examiner* — Tran M. Tran
(74) *Attorney, Agent, or Firm* — Muir Patent Law, PLLC

(57) ABSTRACT

Provided is a contaminant analysis apparatus including a pretreatment sampler configured to collect and filter an effluent discharged through a discharge pipe to provide an analysis target sample, a sample introduction unit configured to receive the analysis target sample from the pretreatment sampler, a sample injection unit configured to selectively supply the analysis target sample supplied from the sample introduction unit, a sample analysis unit including an integrated analyzer configured to analyze ion components and heavy metal components of the analysis target sample which is supplied from the sample injection unit, and an analysis controller configured to control the sample introduction unit, the sample injection unit, and the sample analysis unit, wherein the sample introduction unit includes a first sample introduction unit including two or more first sample introduction unit syringe pumps and a second sample introduction unit including one or more second sample introduction unit syringe pumps.

19 Claims, 9 Drawing Sheets

(56) References Cited

U.S. PATENT DOCUMENTS

| | | | | |
|---|---|---|---|---|
| 5,538,689 | A * | 7/1996 | Dybdahl | G01N 33/182 436/161 |
| 5,567,619 | A * | 10/1996 | Stone | G01N 33/84 436/175 |
| 5,646,863 | A * | 7/1997 | Morton | G01N 33/18 210/85 |
| 5,824,270 | A * | 10/1998 | Rao | G01N 21/78 422/62 |
| 6,470,760 | B2 * | 10/2002 | Shinozaki | G01N 1/22 422/89 |
| 8,758,587 | B2 * | 6/2014 | Sugiyama | G01N 27/44743 422/50 |
| 9,408,556 | B2 * | 8/2016 | Wang | G01N 33/497 |
| 9,410,928 | B2 * | 8/2016 | Murthy | G01N 33/1813 |
| 9,804,076 | B2 * | 10/2017 | Harrell | G01N 17/00 |
| 10,403,117 | B2 * | 9/2019 | Song | G01N 33/1813 |
| 10,465,853 | B2 | 11/2019 | Wiederin et al. | |
| 10,479,698 | B2 * | 11/2019 | Dajani | C02F 1/008 |
| 10,976,294 | B2 * | 4/2021 | Saini | B03C 1/282 |
| 11,162,933 | B2 * | 11/2021 | Chatterjee | C02F 1/004 |
| 11,385,208 | B2 * | 7/2022 | Nogami | G01N 30/24 |
| 11,906,407 | B2 * | 2/2024 | Nishimura | G01N 33/1893 |
| 11,964,882 | B2 * | 4/2024 | Cho | G01N 21/3577 |
| 11,965,838 | B2 * | 4/2024 | Nissinen | G01N 1/405 |
| 11,971,375 | B2 * | 4/2024 | Dong | G01N 24/08 |
| 11,971,398 | B2 * | 4/2024 | Hill | G01N 33/182 |
| 12,025,603 | B2 * | 7/2024 | Tsutano | B01J 39/20 |
| 12,061,182 | B2 * | 8/2024 | Al-Tawfiq | G01N 27/333 |
| 12,158,415 | B2 * | 12/2024 | Cheramy | G01N 33/1826 |
| 12,332,268 | B2 * | 6/2025 | Strande | G01N 21/553 |
| 12,474,295 | B2 * | 11/2025 | Matsushita | G01N 27/4163 |
| 12,487,222 | B2 * | 12/2025 | Hanko | G01N 35/1097 |
| 12,504,415 | B2 * | 12/2025 | Lim | G01N 33/18 |
| 2005/0010002 | A1 * | 1/2005 | Shibukawa | G01N 33/1813 525/515 |
| 2005/0129575 | A1 * | 6/2005 | Partridge | G01N 33/1813 422/62 |
| 2007/0278096 | A1 * | 12/2007 | Viltchinskaia | G01N 33/1813 204/434 |
| 2009/0286323 | A1 * | 11/2009 | Yamamoto | G01N 33/1813 436/83 |
| 2011/0284395 | A1 * | 11/2011 | Dimitrakopoulos | G01N 27/42 204/406 |
| 2016/0272506 | A1 * | 9/2016 | Jensen | A01C 23/007 |
| 2017/0276296 | A1 * | 9/2017 | Wiederin | F15D 1/06 |
| 2019/0219539 | A1 * | 7/2019 | Huang | G01N 1/44 |
| 2019/0383840 | A1 * | 12/2019 | Wiederin | G01N 35/00732 |
| 2022/0032297 | A1 * | 2/2022 | Doungmene | G01N 27/49 |
| 2022/0065839 | A1 | 3/2022 | Kitada | |
| 2022/0276215 | A1 | 9/2022 | Nagao | |
| 2026/0028254 | A1 * | 1/2026 | Sajdak | C02F 1/441 |

FOREIGN PATENT DOCUMENTS

| | | | |
|---|---|---|---|
| JP | 7119400 | B2 | 8/2022 |
| KR | 10-0562478 | B1 | 3/2006 |
| KR | 10-0896044 | B1 | 5/2009 |
| KR | 10-0955710 | B1 | 5/2010 |
| KR | 10-1035031 | B1 | 5/2011 |
| KR | 10-1596727 | B1 | 2/2016 |
| KR | 10-1710859 | B1 | 3/2017 |
| KR | 10-2046330 | B1 | 11/2019 |
| KR | 10-2150683 | B1 | 9/2020 |
| WO | 2020-144902 | A1 | 7/2020 |

* cited by examiner

FIG. 9

| | Cl(ppm) | $SO_4$(ppm) |
|---|---|---|
| PREVIOUS DATA | 400 | 400 |
| ANALYSIS DATA | 886.93 | 552.09 |
| REANALYSIS DATA | 857.98 | 564.10 |

CONTAMINANT ANALYSIS APPARATUS AND WATER QUALITY MONITORING SYSTEM

CROSS-REFERENCE TO RELATED APPLICATION

This application is based on and claims priority under 35 U.S.C. § 119 to Korean Patent Application No. 10-2023-0017033, filed on Feb. 8, 2023, in the Korean Intellectual Property Office, the disclosure of which is incorporated by reference herein in its entirety.

BACKGROUND

A large amount of wastewater contaminated with gases and chemicals is generated in the semiconductor manufacturing process, and each manufacturing line that discharges the wastewater must safely purify (e.g., remove at least a portion of the gases and chemicals) the wastewater through a separate purification process before the wastewater is released as effluent. The ion components and heavy metal components that may be included in these effluents are managed as a subject of periodic monitoring. However, equipment for ion component analysis and equipment for heavy metal component analysis take up valuable facility space and require additional maintenance.

In addition, due to problems such as a high level of suspended solids in manufacturing process emissions, the frequency of abnormal data, such as a sharp increase or a sharp drop in a measured concentration of a metal component or an ion component in the effluent may be high during analysis.

SUMMARY

Embodiments of the inventive concept provide a contaminant analysis apparatus and a real-time water quality monitoring system capable of purifying wastewater generated from a semiconductor manufacturing line and monitoring the discharged effluent in real-time.

Embodiments of the inventive concept provide a contaminant analysis apparatus and a real-time water quality monitoring system in which a sample analysis unit recognizes abnormal data and reanalyzes a sample in which abnormal data occurs when abnormal data is generated during semiconductor wastewater analysis compared to the trend.

Embodiments of the inventive concept provide a contaminant analysis apparatus and a real-time water quality monitoring system in which an ion analysis unit is integrated with a heavy metal analysis unit.

According to an aspect of the inventive concept, there is provided a contaminant analysis apparatus that acquires and analyzes a sample from effluent discharged through a discharge pipe where the effluent is wastewater generated from semiconductor manufacturing lines that has been purified, the contaminant analysis apparatus including a pretreatment sampler configured to collect and filter an effluent discharged through the discharge pipe to provide an analysis target sample, a sample introduction unit configured to receive the analysis target sample from the pretreatment sampler, a sample injection unit configured to selectively supply the analysis target sample supplied from the sample introduction unit, a sample analysis unit including an integrated analyzer configured to analyze ion components and heavy metal components of the analysis target sample which is supplied from the sample injection unit and to determine whether the analysis target sample is normal or abnormal, and an analysis controller configured to control the sample introduction unit, the sample injection unit, and the sample analysis unit, wherein the sample introduction unit includes a first sample introduction unit including two or more first sample introduction unit syringe pumps and a second sample introduction unit including one or more second sample introduction unit syringe pumps.

According to another aspect of the inventive concept, there is provided a real-time water quality monitoring system including a plurality of wastewater treatment facilities configured to purify wastewater generated from semiconductor manufacturing lines, and a plurality of contaminant analysis apparatuses configured to obtain and analyze samples from effluent discharged through the discharge pipes of each of the wastewater treatment facilities, wherein each of the plurality of contaminant analysis apparatuses include a pretreatment sampler configured to collect and filter the effluent discharged through the discharge pipe to provide an analysis target sample, a sample introduction unit configured to receive the analysis target sample from the pretreatment sampler, a sample injection unit configured to selectively supply the analysis target sample supplied from the sample introduction unit, a sample analysis unit including an integrated analyzer for analyzing ion components and heavy metal components of the analysis target sample which is supplied from the sample injection unit and to determine whether the analysis target sample is normal or abnormal, and an analysis controller configured to control the sample introduction unit, the sample injection unit, and the sample analysis unit, wherein the sample introduction unit includes a heavy metal sample introduction unit including a first syringe pump and a second syringe pump and an ion sample introduction unit including one or more ion syringe pumps.

According to another aspect of the inventive concept, there is provided a contaminant analysis apparatus t including a pretreatment sampler configured to collect and filter effluent discharged through a discharge pipe to provide an analysis target sample, a sample introduction unit configured to supply the analysis target sample from the pretreatment sampler, a sample injection unit configured to selectively supply the analysis target sample supplied through the sample line, a sample analysis unit having an integrated analyzer configured to analyze ion components and heavy metal components of the analysis target sample supplied from the sample introduction unit and to determine whether the analysis target sample is normal or abnormal, and an analysis controller configured to control the sample introduction unit, the sample injection unit, and the sample analysis unit to reanalyze a second analysis target sample identical to the first analysis target sample in response to the sample analysis unit determining that the first analysis target sample is abnormal.

BRIEF DESCRIPTION OF THE DRAWINGS

Embodiments will be more clearly understood from the following detailed description taken in conjunction with the accompanying drawings in which:

FIG. 9 is a table for explaining a sample analysis method using a contaminant analysis apparatus according to some embodiments of the inventive concept.

DETAILED DESCRIPTION

Figure 1:
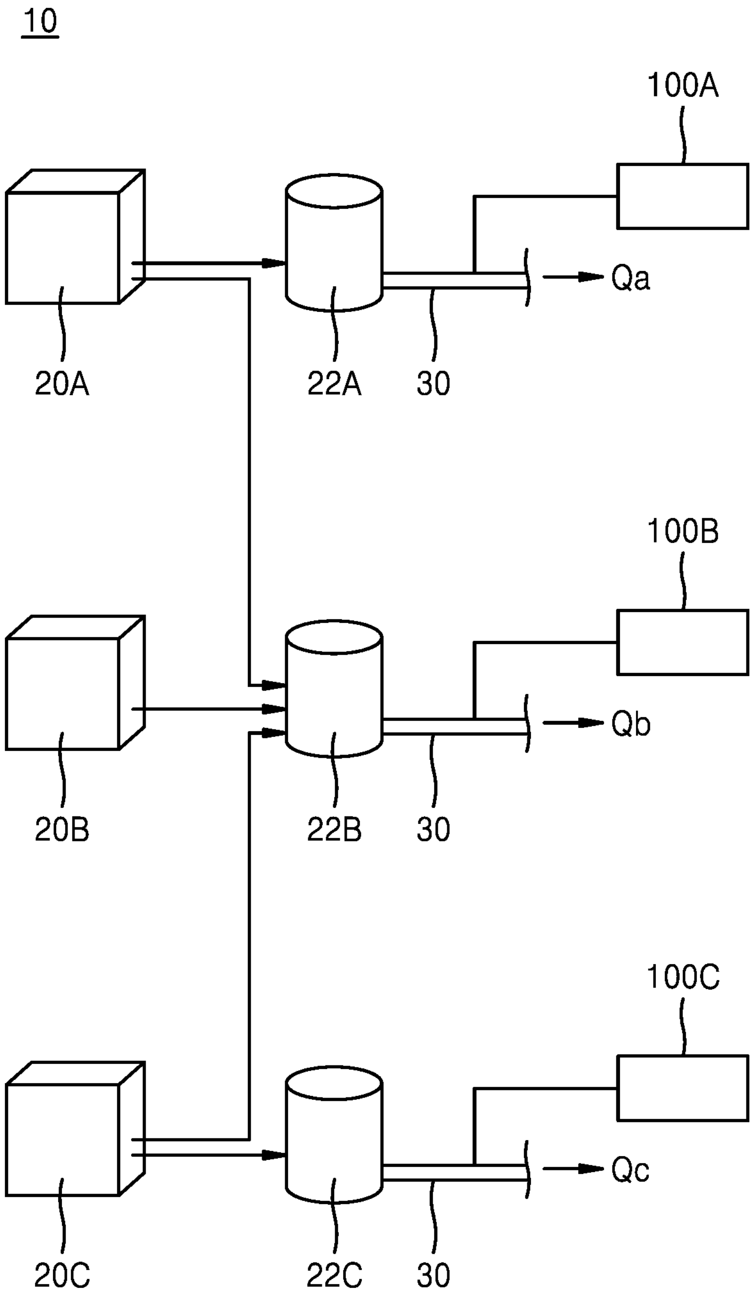
FIG. 1 is a block diagram showing a semiconductor manufacturing system including a water quality monitoring system according to an embodiment of the inventive concept.

Hereinafter, embodiments of the inventive concept will be described in detail with reference to the accompanying drawings. The same reference numerals are used for the same components in the drawings, and duplicate descriptions thereof are omitted. In the following description ordinal numbers such as "first," "second," "third," etc. may be used simply as labels of certain elements, steps, etc., to distinguish such elements, steps, etc. from one another. Terms that are not described using "first," "second," etc., in the specification, may still be referred to as "first" or "second" in a claim. In addition, a term that is referenced with a particular ordinal number (e.g., "first" in a particular claim) may be described elsewhere with a different ordinal number (e.g., "second" in the specification or another claim). Unless otherwise indicated, the use of an ordinal number does not indicate any particular order of items associated with the ordinal number.

FIG. 1 is a diagram showing a semiconductor manufacturing system that includes a water quality monitoring system according to an embodiment of the inventive concept.

Figure 2:
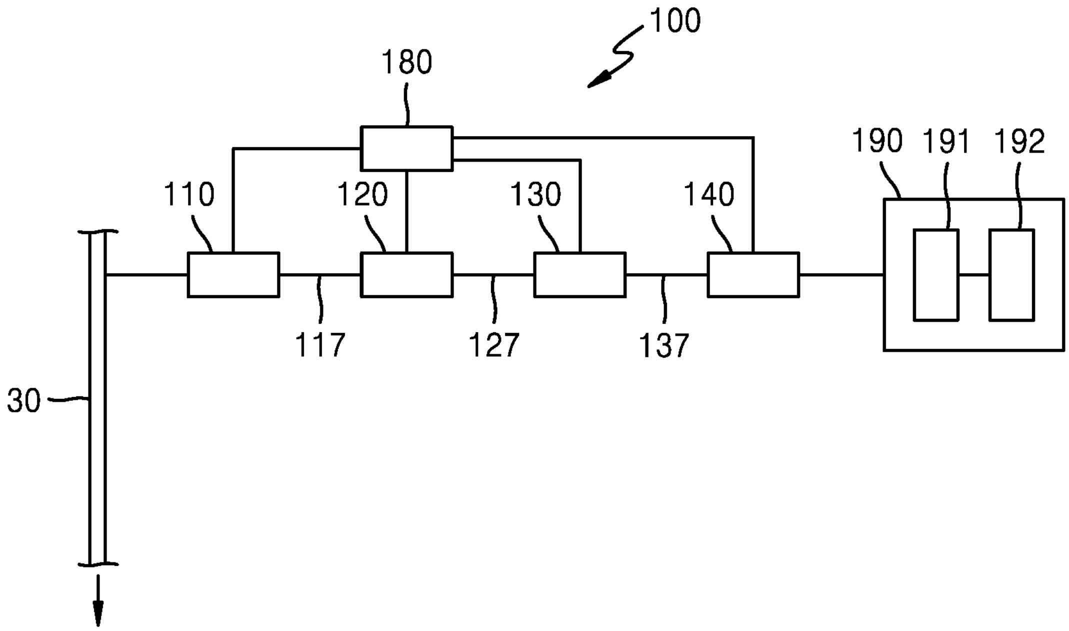
FIG. 2 is a block diagram illustrating a contaminant analysis apparatus according to an embodiment of the inventive concept.

FIG. 2 is a diagram illustrating a contaminant analysis apparatus according to an embodiment of the inventive concept.

Referring to FIGS. 1 and 2, a semiconductor manufacturing system 10 may include a plurality of wastewater treatment facilities 22A, 22B, and 22C for purifying wastewater generated from semiconductor manufacturing lines 20A, 20B, and 20C, and contaminant analysis apparatuses 100A, 100B, and 100C for analyzing contaminants in the effluent discharged from the plurality of wastewater treatment facilities 22A, 22B, and 22C. The wastewater treatment facilities 22A, 22B, and 22C and the contaminant analysis apparatuses 100A, 100B, and 100C may together comprise a water quality monitoring system.

In the semiconductor manufacturing lines 20A, 20B, and 20C, a large amount of wastewater may be generated due to gases, chemicals, and the like used in manufacturing processes. Wastewater generated from each of the semiconductor manufacturing lines 20A, 20B, and 20C may be collected by the plurality of wastewater treatment facilities 22A, 22B, and 22C and purified through separate purification treatment processes.

The wastewater generated in the semiconductor manufacturing lines 20A, 20B, and 20C may be collected in wastewater tanks of the wastewater treatment facilities 22A, 22B, and 22C, respectively. The wastewater may be purified by a purification treatment process to produce purified water that may be collected in a discharge tank and eventually discharged through discharge pipes 30 of the wastewater treatment facilities 22A, 22B, and 22C as effluent. The contaminant analysis apparatuses 100A, 100B, and 100C may obtain and analyze samples from the effluent discharged through the discharge pipes 30 from the wastewater treatment facilities 22A, 22B, and 22C, respectively.

For example, wastewater collected into a wastewater tank may be purified by an inorganic primary treatment process, an organic treatment process, and an inorganic secondary treatment process. In the inorganic primary treatment process, the pH of the wastewater may be adjusted through chemical treatment using chemicals and precipitates in wastewater may be removed. In the organic treatment process, organic substances in the wastewater may be removed using microorganisms. In the inorganic secondary treatment process, the pH of the wastewater may be adjusted to meet a desired specification through chemical treatment using chemicals.

The semiconductor manufacturing lines 20A, 20B, and 20C may be connected to some certain facilities among the wastewater treatment facilities 22A, 22B, and 22C according to the characteristics of the facilities of each manufacturing line and materials to be purified. For example, wastewater generated in the first semiconductor manufacturing line 20A may be supplied to the first and second wastewater treatment facilities 22A and 22B. Wastewater generated in the second semiconductor manufacturing line 20B may be supplied to the second wastewater treatment facility 22B. Wastewater generated in the third semiconductor manufacturing line 20C may be supplied to the second and third wastewater treatment facilities 22B and 22C. Embodiments of the inventive concept are not limited to these connection relationships between semiconductor manufacturing lines and wastewater treatment facilities and the connection relationships may be designed in various ways as needed. Additionally, embodiments of the inventive concept are not limited to the described quantity of semiconductor manufacturing lines and wastewater treatment facilities, and the number of semiconductor manufacturing lines and wastewater treatment facilities may not be equal.

As shown in FIG. 2, each of the contaminant analysis apparatuses 100A, 100B, and 100C may include a pretreatment sampler 110, a sample introduction unit 120, a sample injection unit 130, a sample analysis unit 140, and a monitoring device 190. The monitoring device 190 may include a monitor controller 191 and a monitoring unit 192.

Each of the contaminant analysis apparatuses 100A, 100B, and 100C may include components such as pumps, valves, pipes, sensors, etc. suitable for collecting an analysis target sample (e.g., a sample of the effluent) from the effluent discharged through the discharge pipes 30, collecting a reference sample from a reference sample feeder, and transferring any one of the collected samples to the sample analysis unit 140. In some embodiments, the contaminant analysis apparatuses 100A, 100B, and 100C may include a storage tank for collecting discharged effluent. In addition, each of the contaminant analysis apparatuses 100A, 100B, and 100C may further include an analysis controller 180 configured to control the sample introduction unit 120, the sample injection unit 130, and the sample analysis unit 140. For example, the analysis controller 180 may control operations of components such as pumps and valves through control signals originated by the analysis controller 180 to cause the components to perform operations.

Although not illustrated, a controller, such as the analysis controller 180 or the monitor controller, can include one or more of the following components: at least one central processing unit (CPU) configured to execute computer program instructions to perform various processes and methods, random access memory (RAM) and read only memory (ROM) configured to access and store data and information and computer program instructions, input/output (I/O) devices configured to provide input and/or output to the processing controller 1020 (e.g., keyboard, mouse, display, speakers, printers, modems, network cards, etc.), and storage media or other suitable type of memory (e.g., such as, for example, RAM, ROM, programmable read-only memory (PROM), erasable programmable read-only memory (EPROM), electrically erasable programmable read-only memory (EEPROM), magnetic disks, optical disks, floppy disks, hard disks, removable cartridges, flash drives, any type of tangible and non-transitory storage medium) where data and/or instructions can be stored. In addition, the controller can include antennas, network interfaces that provide wireless and/or wire line digital and/or analog interface to one or more networks over one or more network connections (not shown), a power source that provides an appropriate alternating current (AC) or direct current (DC) to power one or more components of the controller, and a bus that allows communication among the various disclosed components of the controller.

The pretreatment sampler 110 may be part of a multi-stage filtering process. The pretreatment sampler 110 may sample the effluent and filter the sampled effluent to produce an analysis target sample. The pretreatment sampler 110 may supply the analysis target sample filtered from the effluent to the sample introduction unit 120 through the analysis target sample line 117. The pretreatment sampler 110 may remove floating substances in the effluent discharged from the wastewater purification treatment facility, filter the effluent using filtration suitable for the analysis facility to prevent clogging in the analysis apparatus and reduce the maintenance cost (e.g., reduce the amount of required maintenance) of the analysis target sample line 117.

The pretreatment sampler 110 may receive a reference sample from the reference sample feeder.

The sample introduction unit 120 may selectively supply the analysis target sample filtered by the pretreatment sampler 110 and the reference sample from the reference sample feeder to the sample injection unit 130 through the sample line 127. The sample injection unit 130 of the contaminant analysis apparatus 100 may supply the sample (e.g., either the analysis target sample or the reference sample) supplied by the sample introduction unit 120 to the sample analysis unit 140 through the sample analysis line 137. As described below, the contaminant analysis apparatuses 100A, 100B, and 100C may generate data from the analysis of the analysis target sample and reanalyze hunting data (e.g., abnormal data) that occurs during the analysis of the analysis target sample. Hunting data may be monitored data (e.g., data from the analysis of the analysis target sample) that exceeds a reference value and bounces.

The sample analysis unit 140 may include a heavy metal component analyzer as a first analyzer and an ion component analyzer as a second analyzer. The heavy metal component analyzer may be configured to detect heavy metal components of contaminants contained in a sample and the ion component analyzer may be configured to detect the ion component of the contaminants contained in a sample. Therefore, the contaminant analysis apparatus 100 promotes space efficiency and operational efficiency by including both the heavy metal component analyzer and the ion component analyzer as an integrated analyzer that simultaneously analyzes the ion component and heavy metal component of the contaminant included in the effluent.

Each of the contaminant analysis apparatuses 100A, 100B, and 100C may include a monitoring device 190. The monitoring device 190 may receive analysis result values generated by the contaminant analysis apparatuses 100A, 100B, and 100C that represent the heavy metal components and the ion component of the contaminant. The monitor controller 191 of the monitoring device 190 may receive analysis result values from the contaminant analysis apparatuses 100A, 100B, and 100C through wireless communication and store the analysis result values. The monitoring unit 192 of the monitoring device 190 may monitor the analysis result values representing the concentration of heavy metals and/or ions discharged into the storage tank.

Figure 3:
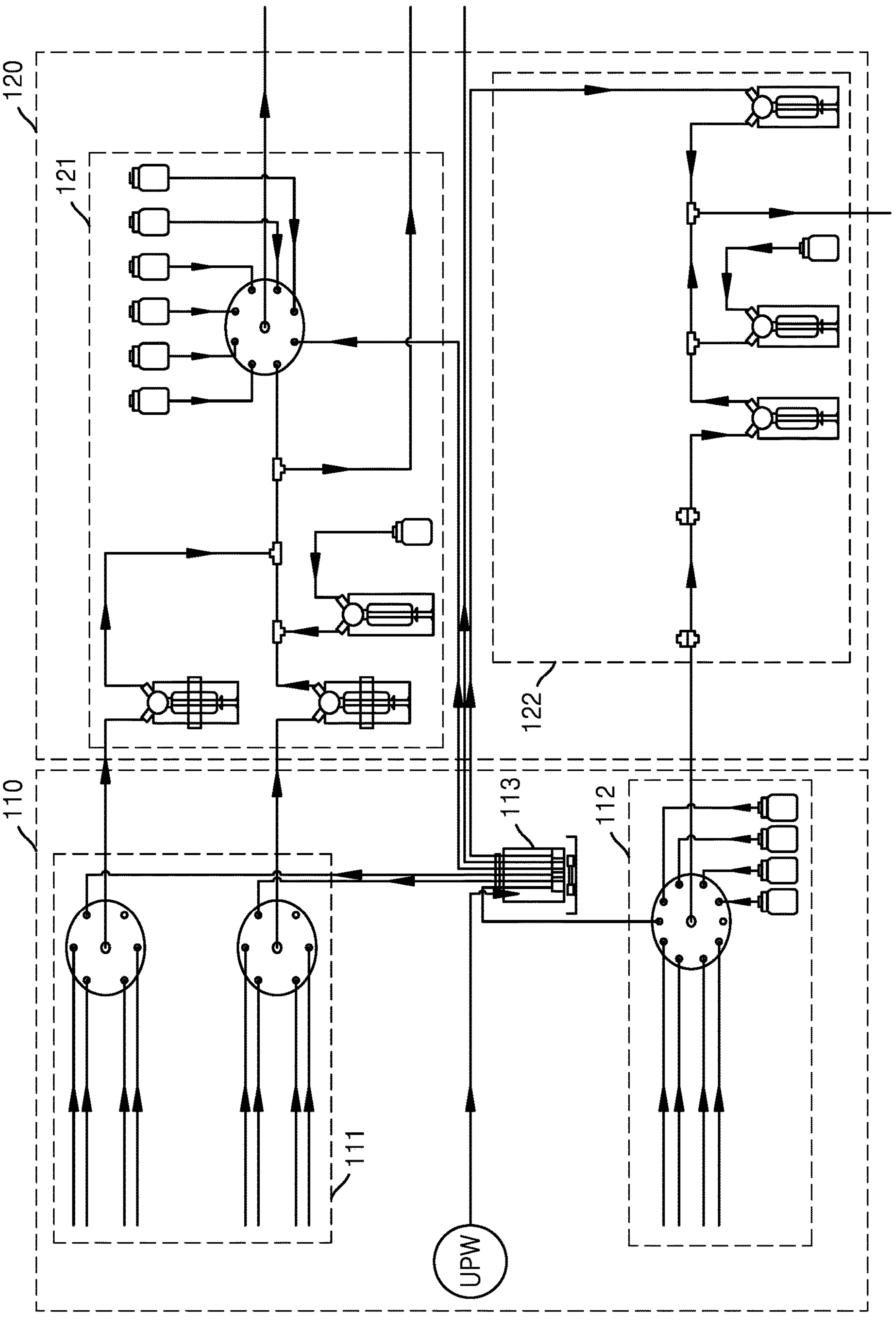
FIG. 3 is a diagram illustrating a pretreatment sampler and a sample introduction unit of a contaminant analysis apparatus according to an embodiment of the inventive concept.

FIG. 3 is a diagram illustrating a pretreatment sampler and a sample introduction unit of a contaminant analysis apparatus according to an embodiment of the inventive concept.

Referring to FIG. 3, the pretreatment sampler 110 of the contaminant analysis apparatus 100 according to embodiments of the inventive concept may include a heavy metal sampler unit 111 and an ion sampler unit 112. The sample introduction unit 120 of the contaminant analysis apparatus 100 according to embodiments of the inventive concept may include a first sample introduction unit such as a heavy metal sample introduction unit 121 and a second sample introduction unit such as an ion sample introduction unit 122. Components associated with the first sample introduction unit may be referred to as first sample introduction components and components associated with the second sample introduction unit may be referred to as second sample introduction components. The contaminant analysis apparatus 100 according to embodiments of the inventive concept promotes space efficiency and operational efficiency by integrating a heavy metal analysis apparatus and an ion analysis apparatus into one facility.

The pretreatment sampler 110 may include a heavy metal sampler unit 111, an ion sampler unit 112, and an ultrapure water generator 113. The ultrapure water generator 113 may be connected to the heavy metal sampler unit 111 and the ion sampler unit 112. The ultrapure water generator 113 may supply ultrapure water (UPW) as a diluent to the ion sample introduction unit 122 or the like via the ion sampler unit 112 or the like. A sample may be diluted with the UPW and flow along the sample line 127 to the sample analysis unit 140 via the sample injection unit 130. Also, the UPW may be used for cleaning the sample line 127.

The heavy metal sampler unit 111 and the ion sampler unit 112 may be fluidly connected to the heavy metal sample introduction unit 121 and the ion sample introduction unit 122, respectively. For example, the heavy metal sample introduction unit 121 may be fluidly connected to the heavy metal sampler unit 111 to selectively supply an analysis target sample, which may be referred to as a heavy metal sample when supplied to the heavy metal sample introduction unit 121, and a reference sample to the sample injection unit 130 through the sample line 127. The ion sample introduction unit 122 may be fluidly connected to the ion sampler unit 112 to selectively supply an analysis target sample, which may be referred to as an ion sample when supplied to ion sample introduction unit 122, and a reference sample to the sample injection unit 130 through the sample line 127. It will be understood that when an element is referred to as being "connected" or "coupled" to or "on" another element, it can be directly connected or coupled to or on the other element or intervening elements may be present. As used herein, items described as being "fluidly connected" are configured such that a liquid or gas can flow, or be passed, from one item to the other. The configuration of each of the pretreatment sampler 110 and the sample introduction unit 120 is described in detail below.

Figure 4:
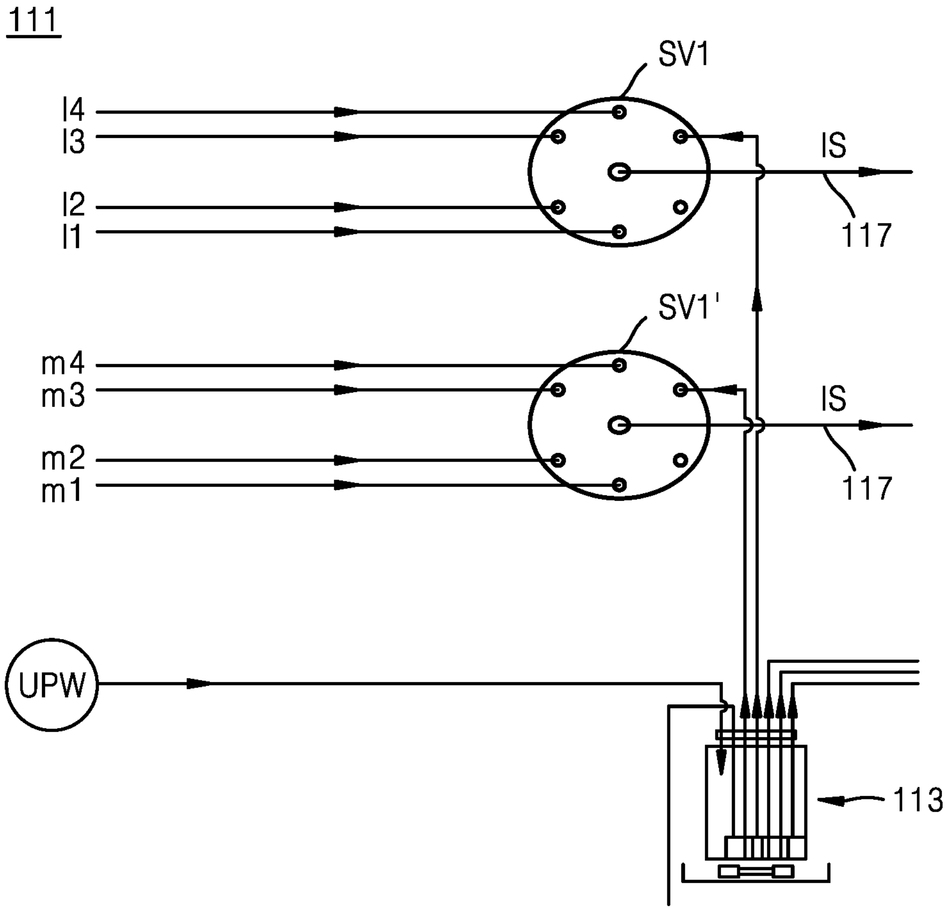
FIG. 4 is a view showing a heavy metal sampler part of the pretreatment sampler of FIG. 2.

FIG. 4 is a view showing a heavy metal sampler part of the pretreatment sampler 110 of FIG. 2.

Referring to FIG. 4, the heavy metal sampler unit 111 of the contaminant analysis apparatus 100 according to embodiments of the inventive concept may include first switching valves SV1 and SV1' and a plurality of sampling port lines L1 to L4 and m1 to m4.

The pretreatment sampler 110 may include a multi-stage filter system having a filter for removing suspended matter or the like in the effluent. The multi-stage filter system may be cylindrical in shape to accommodate the effluent. A sampling inlet tube communicates with the discharge pipe or the effluent tank to introduce the effluent discharged therefrom into the multi-stage filter system. The multi-stage filter system may include a sieve installed in the storage tank and an intermediate filter installed in the sampling tube.

The first switching valves SV1 and SV1' may supply the filtered effluent to the sample injection unit 130 as an analysis target sample IS. The first switching valves SV1 and SV1' may be fluidly connected to first to fourth sampling port lines L1 to L4 and m1 to m4, respectively, for supplying effluent from the storage tank. By the operation of the first switching valves SV1 and SV1', the analysis target sample IS may be supplied to the analysis target sample line 117 through a sampling port line selected from among the first to fourth sampling port lines L1 to L4 and m1 to m4.

In addition, a cleaning solution (e.g., UPW) supplied from the ultrapure water generator 113 may be supplied to the analysis target sample line 117 by the operation of the first switching valves SV1 and SV1'.

According to one embodiment, the heavy metal sampler unit 111 of the contaminant analysis apparatus 100 of the inventive concept may include two first switching valves SV1 and SV1' and two groups of sampling port lines L1 to l4 and m1 to m4. One first switching valve SV1 may be connected to a group of sampling port lines L1 to L4, and another first switching valve SV1' may be connected to another group of sampling port lines L1 to L4. Embodiments of the inventive concept are not limited to the described number and connection relationship of the first switching valves and the sampling port lines and the number and connection relationships may be designed in various ways as needed.

The heavy metal sampler unit 111 includes two first switching valves SV1 and SV1' and a plurality of sampling port lines L1 to L4 and m1 to m4 and may thus be connected to syringe pumps of the heavy metal sample introduction unit 120 to be described below. A description of the heavy metal sample introduction unit 120 is described in detail below.

Figure 5:
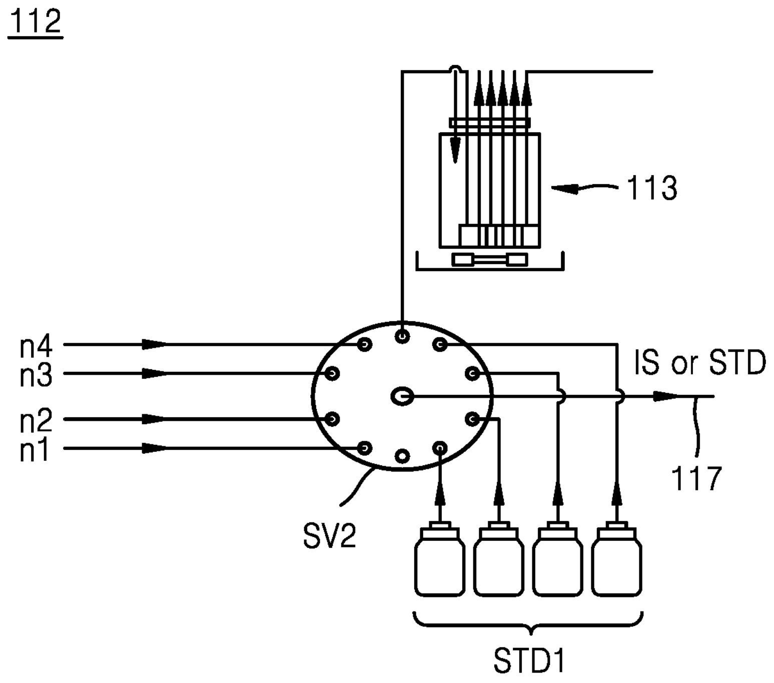
FIG. 5 is a view showing an ion sampler unit of the pretreatment sampler of FIG. 2.

FIG. 5 is a view showing an ion sampler unit of the pretreatment sampler of FIG. 2.

Referring to FIG. 5, the ion sampler unit 112 of the contaminant analysis apparatus 100 of the inventive concept may include a second switching valve SV2 and a plurality of sampling port lines n1 to n4.

The second switching valve SV2 may supply the filtered effluent from the pretreatment sampler 110 to the sample injection unit 130 as an analysis target sample IS. The second switching valve SV2 may be fluidly connected to the first to fourth sampling port lines n1 to l4 for supplying effluent to the sample injection unit 130, respectively. By the operation of the second switching valve SV2, the analysis target sample IS may be supplied to the analysis target sample line 117 through a sampling port line selected from among the first to fourth sampling port lines n1 to n4.

The second switching valve SV2 may be connected to a first reference sample supply unit STD1. The second switching valve SV2 may supply any one of the analysis target sample IS and a reference sample supplied from the first reference sample supply unit STD1 to the sample introduction unit 120 through the analysis target sample line 117. In addition, a dilution solution (e.g., UPW) supplied from the ultrapure water generator 113 may be supplied to the analysis target sample line 117 by the operation of the second switching valve SV2.

Figure 6:
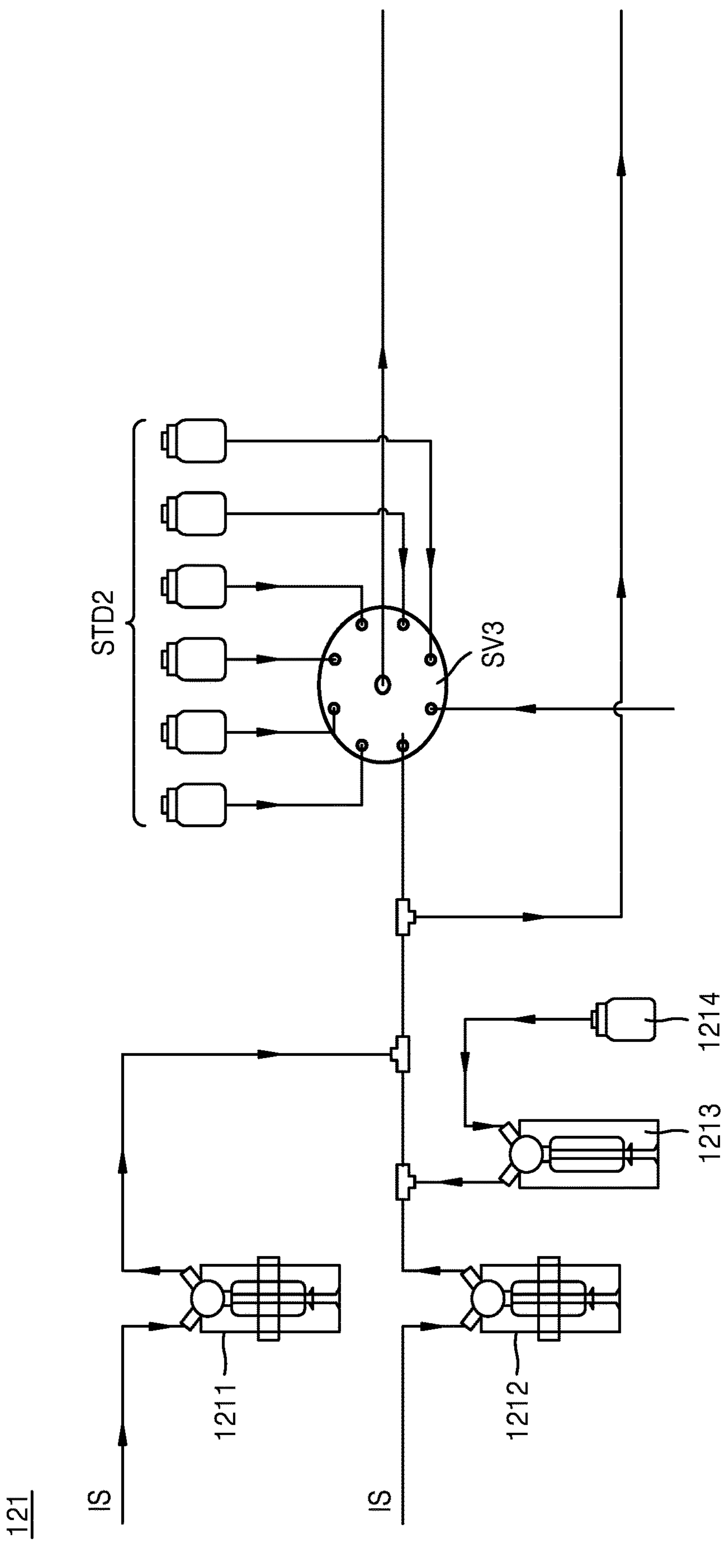
FIG. 6 is a view showing a heavy metal sample introduction unit of a sample introduction unit of FIG. 2.

FIG. 6 is a view showing a heavy metal sample introduction unit of the sample introduction unit of FIG. 2.

Referring to FIG. 6, the heavy metal sample introduction unit 121 of the contaminant analysis apparatus 100 according to embodiments of the inventive concept may include a plurality (e.g., two or more) of syringe pumps 1211, 1212, and 1213 and a third switching valve SV3. The syringe pumps 1211, 1212, and 1213 are pumps that operate using a syringe principle, and may be pumps that precisely control the intake and output of samples such as heavy metals and/or ions according to reciprocating movements of a plunger of the syringe pump.

The first syringe pump 1211 may be connected to one first switching valve SV1 of the heavy metal sampler unit 111. The second syringe pump 1212 may be connected to another first switching valve SV1' of the heavy metal sampler unit 111. Also, the first syringe pump 1211 and the second syringe pump 1212 may be fluidly connected to the third switching valve SV3. The third switching valve SV3 may be connected to the second reference sample supply unit STD2.

The heavy metal sample introduction unit 121 may selectively supply the analysis target sample filtered by the heavy metal sampler unit 111 and the reference sample from the second reference sample supply unit STD2 to the sample injection unit 130 through the sample line via 127.

The first syringe pump 1211 and the second syringe pump 1212 may be configured to supply an analysis target sample and a reference sample to the sample injection unit 130. The first syringe pump 1211 and the second syringe pump 1212 may provide pressure so that the sample flows from the third switching valve SV3 to the sample analysis unit 140 via the sample injection unit 130. The first syringe pump 1211 and the second syringe pump 1212 may be simultaneously driven, concurrently driven, or driven in parallel, so that the first syringe pump 1211 and the second syringe pump 1212 may be filled with an analysis target sample simultaneously, concurrently, or in parallel. In some embodiments, the capacities of the first syringe pump 1211 and the second syringe pump 1212 may be the same. For example, each of the capacities of the first syringe pump 1211 and the second syringe pump 1212 may be 5 ml.

The heavy metal sample introduction unit 121 of the contaminant analysis apparatus 100 of the inventive concept may reanalyze the analysis target sample using the first syringe pump 1211 and the second syringe pump 1212. An analysis target sample stored in one of the first syringe pump 1211 and the second syringe pump 1212 may be analyzed first. If the sample analysis unit 140 determines that the analysis target sample analyzed first results in abnormal data, the analysis target sample stored in another syringe pump may be reanalyzed. When an action is taken based on the results of a determination, the action may be referred to as being in response to the determination. For example, when the sample analysis unit 140 determines that the analysis target sample analyzed first results in abnormal data, the analysis target sample stored in another syringe pump may be reanalyzed in response to the determination.

For example, the first analysis target sample stored in the first syringe pump 1211 may be analyzed. When the sample analysis unit 140 determines that an analysis of the first analysis target sample results in normal data, the analysis controller 180 may control the heavy metal sample introduction unit 121 so that the second analysis target sample stored in the second syringe pump 1212 is discharged through the pipe.

On the other hand, when the sample analysis unit 140 determines that the analysis of the first analysis target sample results in abnormal data, the analysis controller 180 controls the heavy metal sample introduction unit 121 so that the second analysis target sample stored in the second syringe pump 1212 is supplied to the sample analysis unit 140 so that the second analysis target sample may be reanalyzed. By analyzing the first analysis target sample and the second analysis target sample in the sample analysis unit 140, equipment abnormalities of the contaminant analysis apparatus may be confirmed.

The third syringe pump 1213 may be configured to supply a diluent or the like for checking equipment abnormalities of the contaminant analysis apparatus 100. A quality check (QC) analysis of the contaminant analysis apparatus 100 may be performed by receiving a diluent from a diluent supply unit 1214 of the third syringe pump 1213. In this case, the QC analysis may refer to a process of analyzing a standard material at a reference concentration. The diluent may be, for example, bismuth (Bi) or the like.

Figure 7:
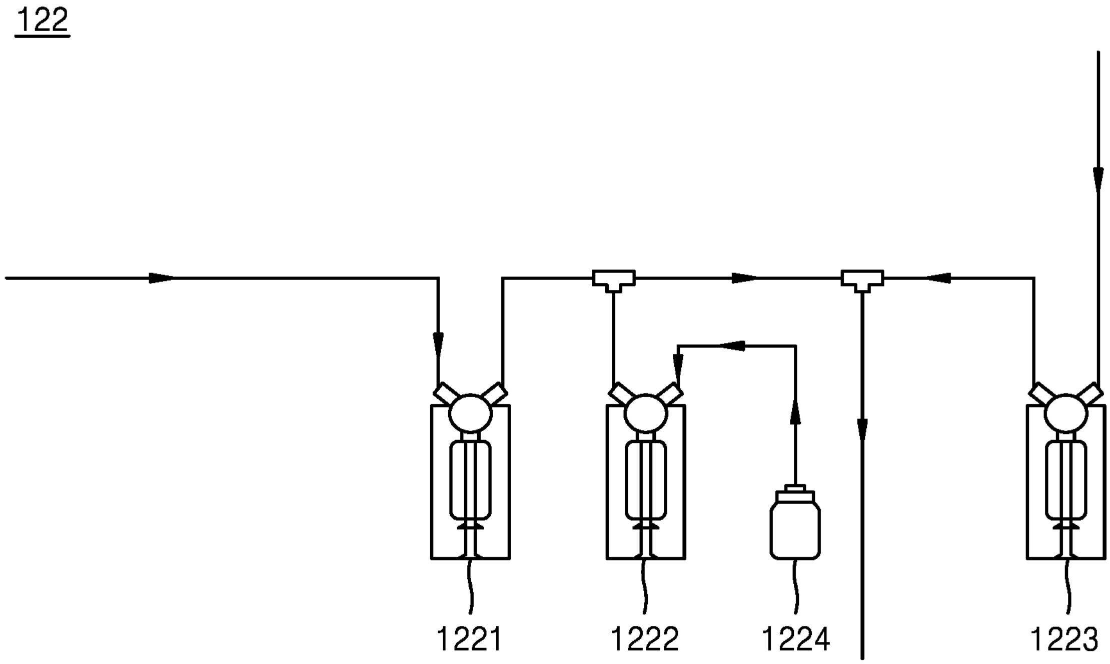
FIG. 7 is a diagram showing an ion sample introduction unit of the sample introduction unit of FIG. 2.

FIG. 7 is a diagram showing an ion sample introduction unit of the sample introduction unit 122 of FIG. 2.

Referring to FIG. 7, the ion sample introduction unit 122 of the contaminant analysis apparatus 100 of the inventive concept may include a plurality of syringe pumps 1221, 1222, and 1223. The syringe pump 1221 may be an ion syringe pump and hereafter referred to as an ion syringe pump.

The ion syringe pump 1221 may selectively supply a sample from one of the analysis target sample filtered by the ion sampler unit 112 and the first reference sample supply unit STD1 to the sample injection unit 130 through the sample line 127. The capacity of the ion syringe pump 1221 may be 2 ml.

The ion sample introduction unit 122 of the contaminant analysis apparatus 100 of the inventive concept may reanalyze the analysis target sample by using the ion syringe pump 1221. At least a part of the analysis target sample stored in the ion syringe pump 1221 may be analyzed first. If the sample analysis unit 140 determines that the previously analyzed analysis target sample is abnormal data, the remaining analysis target sample stored in the ion syringe pump 1221 may be reanalyzed.

The analysis controller 180 may control the sample introduction unit 120 and the sample injection unit 130 so that at least a part of the analysis target sample (hereinafter referred to as 'remaining analysis target sample') is left in the ion syringe pump 1221, and the rest of the analysis target sample (hereinafter referred to as 'supply analysis target sample') is supplied to the sample analysis unit 140. The analysis controller 180 may control the sample introduction unit 120 so that the supply analysis target sample and the remaining analysis target sample have the same capacity (e.g., volume). For example, the analysis controller 180 may control the sample introduction unit 120 so that the supply analysis target sample and the remaining analysis target sample are each 1 ml.

For example, the sample analysis unit 140 may first analyze a supplied analysis target sample. When the sample analysis unit 140 determines that the supplied analysis target sample is normal, the analysis controller 180 may control the ion sample introduction unit 122 so that the remaining analysis target sample stored in the ion syringe pump 1221 is discharged through the pipe.

On the other hand, if the sample analysis unit 140 determines that the supplied analysis target sample is abnormal, the analysis controller 180 controls the heavy metal sample introduction unit 121 so that the remaining analysis target sample stored in the ion syringe pump 1221 is supplied to the sample analysis unit 140, thereby re-analyzing the remaining analysis target sample. By analyzing the supplied analysis target sample and the remaining analysis target sample in the sample analysis unit 140, equipment abnormalities of the contaminant analysis apparatus may be confirmed.

The remaining syringe pumps 1222 and 1223 may be configured to supply the UPW or diluent to check equipment failure of the contaminant analysis apparatus 100.

Figure 8:
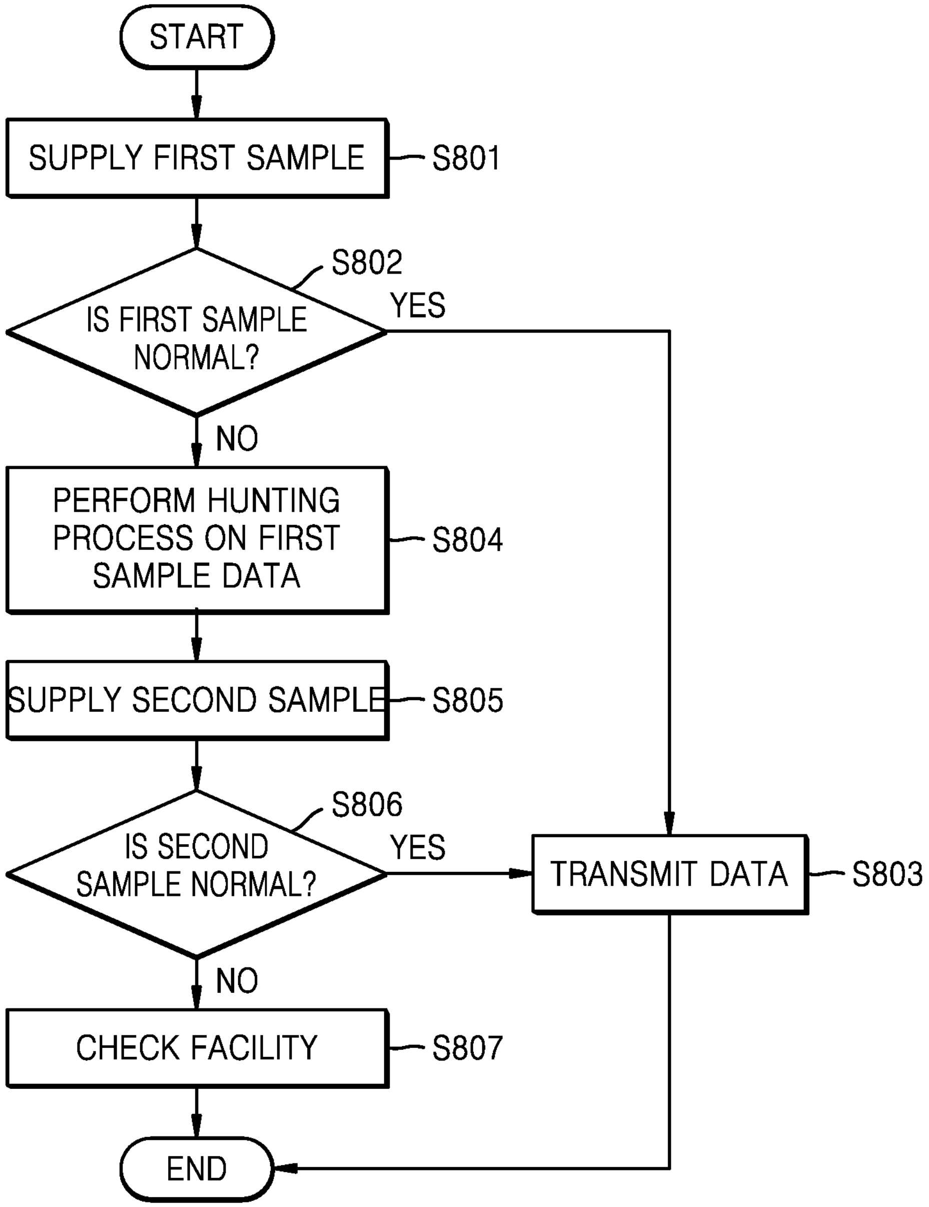
FIG. 8 is a flowchart illustrating a sample analysis process using a contaminant analysis apparatus, according to some embodiments of the inventive concept.

FIG. 8 is a flowchart illustrating a sample analysis process using a contaminant analysis apparatus, according to the inventive concept.

Referring to FIG. 8, a sample analysis process using the contaminant analysis apparatus 100 according to embodiments of the inventive concept may include supplying a first sample in S801. The first sample may be the aforementioned first analysis target sample or supplied analysis target sample.

The sample analysis unit 140 may determine whether the first sample is normal in S802. Whether the first sample is normal may be determined by comparing the first sample with the existing data trend. The sample analysis unit 140 may determine whether the first sample is normal based on a comparison with previous data and % RSD. At this time, % RSD is a value calculated by (standard deviation/average)×100 of the previous data values. For example, it may be a value obtained by calculating (standard deviation/average)×100 data of samples for the last year. The sample analysis unit 140 may set the % RSD value within 5% for ions and set the % RSD value within 10% for heavy metals.

When the % RSD value of the first sample measured by the sample analysis unit 140 is within a set range, the first sample may be regarded as normal data. For example, if the % RSD value of the ion of the first sample is within 5% of the previous data, the first sample may be regarded as normal data. Likewise, if the % RSD value of the heavy metal of the first sample is within 10% of the previous data, the first sample may be regarded as normal data. Accordingly, the data of the first sample, which is considered normal data, may be transmitted to the monitoring device 200 in S803.

When the % RSD value of the first sample measured by the sample analysis unit 140 exceeds a set range, the first sample may be regarded as hunting data in S804. For example, if the % RSD value of the ions of the first sample exceeds 5% of the previous data, the first sample may be regarded as hunting (abnormal) data. Likewise, if the % RSD value of the heavy metal of the first sample exceeds 10 of the previous data, the first sample may be regarded as hunting (abnormal) data. In this case, the hunting data may mean that the monitored data exceeds a reference value and bounces.

When the first sample is processed as hunting data, the sample analysis process using the contaminant analysis apparatus 100 may include supplying a second sample in S805. In this case, the second sample may be the aforementioned second analysis target sample or residual analysis target sample.

The sample analysis unit 140 may determine whether the second sample is normal in S806. Based on the % RSD of the first sample, it may be determined whether the second sample is normal. The sample analysis unit 140 may set the % RSD value within 5% for ions and set the % RSD value within 10% for heavy metals.

When the % RSD value of the second sample measured by the sample analysis unit 140 is within a set range, the second sample may be regarded as normal data. For example, if the % RSD value of ions of the second sample is within 5% of that of the first sample, the second sample may be regarded as normal data. Likewise, if the % RSD value of the heavy metal of the second sample is within 10% of that of the first sample, the second sample may be regarded as normal data. Accordingly, the data of the second sample, which is considered normal data, may be transmitted to the monitoring device 200 in S803.

When the % RSD value of the second sample measured by the sample analysis unit 140 exceeds a set range, the second sample may be regarded as hunting data. For example, if the % RSD value of ions of the second sample exceeds 5% of that of the first sample, the second sample may be regarded as hunting (abnormal) data. Likewise, if the % RSD value of the heavy metal of the second sample exceeds 10% of that of the first sample, the first sample may be regarded as hunting (abnormal) data.

When the second sample is determined to be abnormal, equipment of the contaminant analysis apparatus 100 may be checked in S807. Equipment confirmation of the contaminant analysis apparatus 100 may be performed through QC analysis. In this case, the QC analysis may refer to a process of analyzing a standard material at a reference concentration.

FIG. 9 is a table for explaining a sample analysis method using a contaminant analysis apparatus according to the inventive concept.

Referring to FIG. 9, it may be confirmed that the previous data values of the contaminant analysis apparatus 100 are 400 ppm for Cl and 400 ppm for $SO_4$. When checking the analysis data values measured by the contaminant analysis apparatus 100, it may be confirmed that Cl is 886.93 ppm and $SO_4$ is 552.09 ppm. In this case, the analysis data value may be a value obtained by analyzing the first sample. In the case of ions, it may be seen that the % RSD value compared to the previous data should be within 5%, but the analysis data value exceeds 5%. Accordingly, the contaminant analysis apparatus 100 may consider the first sample as hunting data and perform reanalysis.

When checking the reanalysis data values measured by the contaminant analysis apparatus 100, it may be confirmed that Cl is 857.98 ppm and $SO_4$ is 564.10 ppm. In this case, the reanalysis data value may be a value obtained by analyzing the second sample. It may be seen that the reanalysis data value is within 5% compared to the analysis data value. Accordingly, the second sample is regarded as normal data, and the data of the second sample may be transmitted to the monitoring device 200.

The % RSD may be calculated using the previous data values and the analysis data values. For example, in the case of Cl, the previous data value is 400 and the analysis data value is 886.93. A standard deviation and average values are calculated using the previous data values (400) and the analysis data value (886.93). The % RSD value is about 53% using the standard deviation and average values. Since the % RSD value exceeds 5%, the analysis data may be determined as hunting data. In this case, the analysis data value is 886.93 and the reanalysis data value is 857.98. A standard deviation and average values are calculated using the analysis data value (886.93) and the reanalysis data value (857.98). The % RSD value is about 2% using the standard deviation and average values. Since the % RSD value is less than 5%, the reanalysis data may be determined as normal data.

While the inventive concept has been particularly shown and described with reference to embodiments thereof, it will be understood that various changes in form and details may be made therein without departing from the spirit and scope of the following claims.

What is claimed is:

1. A contaminant analysis apparatus comprising:

a pretreatment sampler configured to collect and filter an effluent discharged through a discharge pipe to provide an analysis target sample;

a first sample introduction unit configured to receive the analysis target sample from the pretreatment sampler, the first sample introduction unit comprising a first heavy metal syringe pump and a second heavy metal syringe pump;

a second sample introduction unit configured to receive the analysis target sample from the pretreatment sampler, the second sample introduction unit including one or more ion syringe pumps;

a sample injection unit configured to selectively supply a sample analysis unit with the analysis target sample supplied from the first sample introduction unit and the second sample introduction unit;

the sample analysis unit including an integrated analyzer configured to analyze ion components and heavy metal components of the analysis target sample supplied from the sample injection unit and to determine that the analysis target sample is abnormal when the heavy metal components fall outside a first range or the ion components fall outside a second range; and an analysis controller configured to control the first sample introduction unit, the second sample introduction unit, the sample injection unit, and the sample analysis unit, wherein the analysis controller is configured to:

control the first sample introduction unit to supply a first portion of the analysis target sample from the first heavy metal syringe pump to the sample injection unit while storing a second portion of the analysis target sample in the second heavy metal syringe pump and to control the second sample introduction unit to supply a third portion of the analysis target sample from the one or more ion syringe pumps to the sample injection unit; and in response to the sample analysis unit determining that the first portion of the analysis target sample is abnormal, control the first sample introduction unit to supply the second portion of the analysis target sample to the sample injection unit.

2. The contaminant analysis apparatus of claim 1, wherein the first heavy metal syringe pump is connected to a first switching valve of the pretreatment sampler, and the second heavy metal syringe pump is connected to a second switching valve of the pretreatment sampler.

3. The contaminant analysis apparatus of claim 2, wherein the capacity of the first heavy metal syringe pump and the capacity of the second heavy metal syringe pump are equal.

4. The contaminant analysis apparatus of claim 2, wherein the analysis controller is configured to control the first sample introduction unit to simultaneously fill the first heavy metal syringe pump and the second heavy metal syringe pump with the analysis target sample.

5. The contaminant analysis apparatus of claim 4, wherein the analysis controller is configured to, in response to the sample analysis unit determining that the first portion of the analysis target sample is normal, control the first sample introduction unit to discharge the second portion of the analysis target sample from the second heavy metal syringe pump.

6. The contaminant analysis apparatus of claim 4, wherein the analysis controller is configured to, in response to the sample analysis unit determining that the first portion of the analysis target sample is abnormal, control the sample analysis unit to analyze the second portion of the analysis target sample.

7. The contaminant analysis apparatus of claim 1, wherein the analysis controller is configured to control the second sample introduction unit so that a fourth portion of the analysis target sample is left in the one or more ion syringe pumps when the third portion of the analysis target sample is supplied to the sample injection unit.

8. The contaminant analysis apparatus of claim 7, wherein the analysis controller is configured to, in response to determining that the third portion of the analysis target sample is normal, control the second sample introduction unit to discharge the fourth portion of the analysis target sample left in the one or more ion syringe pumps.

9. The contaminant analysis apparatus of claim 7, wherein the analysis controller is configured to, in response to the sample analysis unit determining that the third portion of the analysis target sample is abnormal, control the second sample introduction unit to supply the fourth portion of the analysis target sample to the sample injection unit and control the sample analysis unit to analyze the fourth portion of the analysis target sample.

10. The contaminant analysis apparatus of claim 7, wherein the analysis controller is configured to control the second sample introduction unit so that the volume of the third portion of the analysis target sample and the volume of the fourth portion of the analysis target sample are equal.

11. The contaminant analysis apparatus of claim 1,
wherein the first sample introduction unit is a heavy metal sample introduction unit,
wherein the first portion of the analysis target sample and the second portion of the analysis target sample are heavy metal samples,
wherein the second sample introduction unit is an ion sample introduction unit, and wherein the third portion of the analysis target sample is an ion sample.

12. A real-time water quality monitoring system comprising:
a plurality of wastewater treatment facilities configured to purify wastewater generated from semiconductor manufacturing lines; and
a plurality of contaminant analysis apparatuses configured to obtain and analyze samples from effluent discharged through discharge pipes of each of the plurality of wastewater treatment facilities,
wherein each of the plurality of contaminant analysis apparatuses comprises:
a pretreatment sampler configured to collect and filter the effluent discharged through a respective discharge pipe to provide an analysis target sample; a first sample introduction unit configured to receive the analysis target sample from the pretreatment sampler, the first sample introduction unit comprising a first heavy metal syringe pump and a second heavy metal syringe pump;
a second sample introduction unit configured to receive the analysis target sample from the pretreatment sampler, the second sample introduction unit including one or more ion syringe pumps;
a sample injection unit configured to selectively supply a sample analysis unit with the analysis target sample supplied from the first sample introduction unit and the second sample introduction unit;
the sample analysis unit including an integrated analyzer configured to analyze ion components and heavy metal components of the analysis target sample supplied from the sample injection unit and to determine that the analysis target sample is abnormal when the heavy metal components fall outside a first range or the ion components fall outside a second range; and
an analysis controller configured to control the first sample introduction unit, the second sample introduction unit, the sample injection unit, and the sample analysis unit,
wherein the analysis controller is configured to:
control the first sample introduction unit to supply a first portion of the analysis target sample from the first heavy metal syringe pump to the sample injection unit while storing a second portion of the analysis target sample in the second heavy metal syringe pump and to control the second sample introduction unit to supply a third portion of the analysis target sample from the one or more ion syringe pumps to the sample injection unit while storing a fourth portion of the analysis target sample in the one or more ion syringe pumps; and
in response to the sample analysis unit determining that the third portion of the analysis target sample is abnormal, control the second sample introduction unit to supply the fourth portion of the analysis target sample to the sample injection unit.

13. The real-time water quality monitoring system of claim 12, wherein the analysis controller is configured to, in response to determining that the first portion of the analysis target sample is normal, control the first sample introduction unit to discharge the second portion of the analysis target sample.

14. The real-time water quality monitoring system of claim 12,
wherein the analysis controller is configured to, in response to the sample analysis unit determining that the first portion of the analysis target sample is abnormal, control the first sample introduction unit to supply the second portion of the analysis target sample to the sample injection unit and control the sample analysis unit to analyze the second portion of the analysis target sample.

15. The real-time water quality monitoring system of claim 12, wherein the analysis controller is configured to, in response to a determination that the third portion of the analysis target sample is normal, control the second sample introduction unit to discharge the fourth portion of the analysis target sample.

16. The real-time water quality monitoring system of claim 12, wherein the analysis controller is configured to, in response to the sample analysis unit determining that the third portion of the analysis target sample is abnormal, control the second sample introduction unit to supply the fourth portion of the analysis target sample to the sample injection unit and control the sample analysis unit to analyze the fourth portion of the analysis target sample.

17. A contaminant analysis apparatus comprising:

a pretreatment sampler configured to collect and filter an effluent discharged through a discharge pipe to provide an analysis target sample;

a first sample introduction unit configured to receive the analysis target sample from the pretreatment sampler, the first sample introduction unit comprising a first heavy metal syringe pump and a second heavy metal syringe pump;

a second sample introduction unit configured to receive the analysis target sample from the pretreatment sampler, the second sample introduction unit including one or more ion syringe pumps;

a sample injection unit configured to selectively supply the analysis target sample supplied from the first sample introduction unit and the second sample introduction unit;

a sample analysis unit having an integrated analyzer configured to analyze ion components and heavy metal components of the analysis target sample supplied from the sample injection unit and to determine that the analysis target sample is abnormal when the heavy metal components fall outside a first range or the ion components fall outside a second range; and an analysis controller configured to control the first sample introduction unit, the second sample introduction unit, the sample injection unit, and the sample analysis unit, wherein the analysis controller is configured to:

control the first sample introduction unit to supply a first portion of the analysis target sample from the first heavy metal syringe pump to the sample injection unit while storing a second portion of the analysis target sample in the second heavy metal syringe pump and to control the second sample introduction unit to supply a third portion of the analysis target sample from the one or more ion syringe pumps to the sample injection unit while storing a fourth portion of the analysis target sample in the one or more ion syringe pumps;

in response to the sample analysis unit determining that the first portion of the analysis target sample is abnormal, control the first sample introduction unit to supply the second portion of the analysis target sample to the sample injection unit; and in response to the sample analysis unit determining that the third portion of the analysis target sample is abnormal, control the second sample introduction unit to supply the fourth portion of the analysis target sample to the sample injection unit.

18. The contaminant analysis apparatus of claim 17, wherein the first heavy metal syringe pump is connected to a first switching valve of the pretreatment sampler, and the second heavy metal syringe pump is connected to a second switching valve of the pretreatment sampler.

19. The contaminant analysis apparatus of claim 18, wherein the capacity of the first heavy metal syringe pump and the capacity of the second heavy metal syringe pump are equal.

* * * * *